United States Patent [19]
Yokota et al.

[11] Patent Number: 5,846,490
[45] Date of Patent: Dec. 8, 1998

[54] AUTOMATED TEST STRIP SUPPLYING SYSTEM

[75] Inventors: Hiroshi Yokota; Keiji Takahashi, both of Hiratsuka, Japan

[73] Assignee: Bayer Corporation, Elkhart, Ind.

[21] Appl. No.: 678,153

[22] Filed: Jul. 11, 1996

Related U.S. Application Data

[63] Continuation of Ser. No. 422,251, Apr. 14, 1995, abandoned.

[30] Foreign Application Priority Data

May 10, 1994 [JP] Japan .................................. 6-119738

[51] Int. Cl.⁶ .................................................. G01N 35/02
[52] U.S. Cl. ............................. 422/66; 422/63; 422/65; 436/43; 436/46; 436/47; 436/48
[58] Field of Search ................... 422/63–67; 436/43–48, 436/50, 55

[56] References Cited

U.S. PATENT DOCUMENTS

| | | |
|---|---|---|
| 4,279,514 | 7/1981 | Blümel et al. ........................... 356/445 |
| 4,876,204 | 10/1989 | Inoue et al. ................................ 436/46 |
| 5,055,261 | 10/1991 | Khoja et al. ............................... 422/64 |
| 5,097,938 | 3/1992 | Grüner et al. ........................... 198/397 |
| 5,143,694 | 9/1992 | Schäfer et al. ............................ 422/65 |
| 5,209,903 | 5/1993 | Kanamori et al. ......................... 422/65 |
| 5,258,285 | 11/1993 | Egidius ....................................... 435/8 |
| 5,298,425 | 3/1994 | Kuhn et al. ............................... 436/43 |
| 5,415,840 | 5/1995 | Sano et al. ................................ 422/67 |

FOREIGN PATENT DOCUMENTS 0064691  11/1982  European Pat. Off. .

*Primary Examiner*—Long V. Le
*Attorney, Agent, or Firm*—Roger N. Coe

[57] ABSTRACT

Disclosed is an automated supplying system for supplying liquid samples and test strips to an analyzer having a receiving section which receives test strips dipped in liquid samples one by one, a section at which optical characteristics of test pads provided on the received test strips are measured and a section for calculating analytical results of the respective components based on the respective optical characteristics obtained by the measurement.

3 Claims, 3 Drawing Sheets

AUTOMATED TEST STRIP SUPPLYING SYSTEM

This is a continuation of application Ser. No. 08/422,251, filed Apr. 14, 1995, now abandoned.

BACKGROUND OF THE INVENTION

This invention relates to an auxiliary device belonging to the field of clinical chemistry, for dipping test strips one by one in liquid samples such as urine and blood and automatically supplying the dipped test strips successively one by one to a liquid sample analyzer.

More specifically, this invention relates to full automation of a urine analyzer, for example, "CLINITEK® 200+" (trademark of Miles Inc.) manufactured by Miles Inc. by automatically picking up liquid samples and/or test strips from the respective loading portions, dipping the test strips in the liquid samples and then supplying each test strip to the main body of the analyzer by means of the auxiliary device of the present invention.

As one example of conventional liquid sample analyzers, a urine analyzer "CLINITEK 200+" commercially available from Miles Inc. which is an object to which the auxiliary device of the present invention is applied is schematically shown by a dotted line in FIG. 1. The details thereof are disclosed in Japanese Patent Publication No. 20940/1990 (JP-B2-2-20940) and U.S. Pat. Nos. 4,689,202, 4,820,491 and 5,055,261. The other examples of the analyzers are disclosed in Japanese Provisional Patent Publication No. 133960/1993 (JP-A-5-133960), European Patent Publication No. 0 555 771 A1 and U.S. Pat. No. 5,097,938. However, the device of the present invention is not disclosed in the cited prior art.

The conventional CLINITEK 200+ shown in FIG. 1 is a semi-automated analyzer in which analytical operations are carried out after test strips are manually picked up one by one from a test strip bottle (a test strip container) and the test strips (dipped in urine to be analyzed) are manually supplied one by one.

The semi-automated analyzer can measure pH, protein, glucose, a ketone body (acetoacetic acid), bilirubin, occult blood, nitrite, urobilinogen, specific gravity and leukocytes of urine. Its nature is a reflected light photometer which measures tint (color tone) and intensity of reflected light from a portion to be tested which is reacted corresponding to the concentration of a substance (analyte) in urine to be measured.

As shown in FIG. 1, FIG. 2 and FIG. 4, the semi-automated analyzer has roughly divided four parts, i.e., a receiving section 81, a first reading station 82, a second reading station 83 and a waste receiving vessel 84.

The receiving section 81 is a region for receiving test strips after dipping in urine. Each of the first reading station 82 and the second reading station 83 is a region for irradiating light having a predetermined wavelength (or wavelengths) to a plurality of test pads 3 on the test strip 1 (see FIG. 5) and reading the quantity of reflected light in accordance with a reaction rate.

The waste receiving vessel 84 is a receiving box which temporarily contains test strips after reading.

As shown in FIG. 5, in the test strip 1, a plurality of test pads 3 are provided from one end of a transparent or opaque strip 2 made of plastic, and the other end portion is a holding portion 4.

The test pads 3 are formed by pasting filter papers or small pieces of a suitable water-absorptive material which are selectively impregnated with the kinds (numbers) of reagents for the above items to be measured, on the strip 2 by, for example, a double-sided adhesive tape.

The reagents with which the test pads 3 are impregnated are hygroscopic, so that the reagents deteriorate and/or measurement errors occur due to humidity in the air. Thus, as shown in FIG. 6, the reagents on the test strip 1 are kept with a desiccant such as molecular sieves and silica gel in a sample bottle 8, and the sample bottle 8 is tightly closed during storage and transport.

In the conventional semi-automated analyzer to which test strips should be supplied manually one by one, handling of liquid samples and test strips is carried out manually, whereby an operator is fully engaged with the above handling.

Particularly as to the handling of test strips, it is required to repeat cumbersome and simple operations of picking up one test strip, from a plurality of test strips contained in a container tightly closed for preventing humidity, dipping the test strip in a test tube containing a liquid sample, drawing it up from the test tube, removing excess liquid, then correctly positioning and inserting the test strip into a test strip receiving section of an analyzer within a predetermined time and making the analyzer read a result.

In addition, each test strip is treated manually one by one in the same manner, and when the test strips are inserted to the receiving section, it is required to position them correctly, whereby overall operation rate is further limited.

In order to solve the above problem, it may be considered to automate picking up of test strips, dipping of them and supplying of them to a semi-automated analyzer. However, when such automation is attempted to be achieved, there are a number of difficulties to overcome.

The first difficulty is to make a device securely pick up test strips one by one from a plurality of test strips contained in a container tightly closed for preventing humidity, with the right sides thereof facing in one direction, and also position test strips correctly.

The second difficulty is to dip test strips in liquid samples to be tested, draw them up, remove excess liquid and correctly convey and transfer the test strips to a loading region of a semi-automated analyzer within a specific short time.

The third difficulty is to move the auxiliary device of the present invention in synchronization with the operation of a parent device (an analyzer). It is not easy to correctly handle test strips before moistening them with liquid samples and correctly transfer them to the parent device without contaminating them and preventing measurement errors from being caused.

SUMMARY OF THE INVENTION

An object of the present invention is to overcome the above difficulties and realize automation of picking up test strips and/or liquid samples, dipping the test strips and supplying them to a semi-automated analyzer, thereby obtaining high efficiency, high precision and standardization of clinical tests.

That is, the present invention relates to an automated supplying system for supplying liquid samples and test strips to an analyzer having a receiving section which receives test strips dipped in liquid samples one by one, a section at which optical characteristics of test pads provided on the received test strips are measured and a means for calculating analytical results of the respective components (analytes present in the liquid samples) based on the respective optical characteristics obtained by the measurement, which comprises:

a transportation means for passing a plurality of specimen containers containing the liquid samples across a dipping position for dipping in the liquid samples;

a means for picking up the test strips one by one from a test strip container containing a plurality of the test strips;

a overturning means for confirming the right (i.e., correct) side of the picked up test strip and overturning the test strip such that a specific surface may constantly face upward;

a transfer means for receiving the test strip which passes the overturning means, conveying it to the dipping position, dipping it in the liquid sample in one specific specimen container, drawing it out after dipping and then transferring it to the receiving section of the analyzer;

a means for sucking excess liquid sample attached to the test strip drawn out after dipping, in cooperation with the transfer means; and a means for controlling operation timing between movement of the transportation means and movement of the transfer means.

Figure 1:
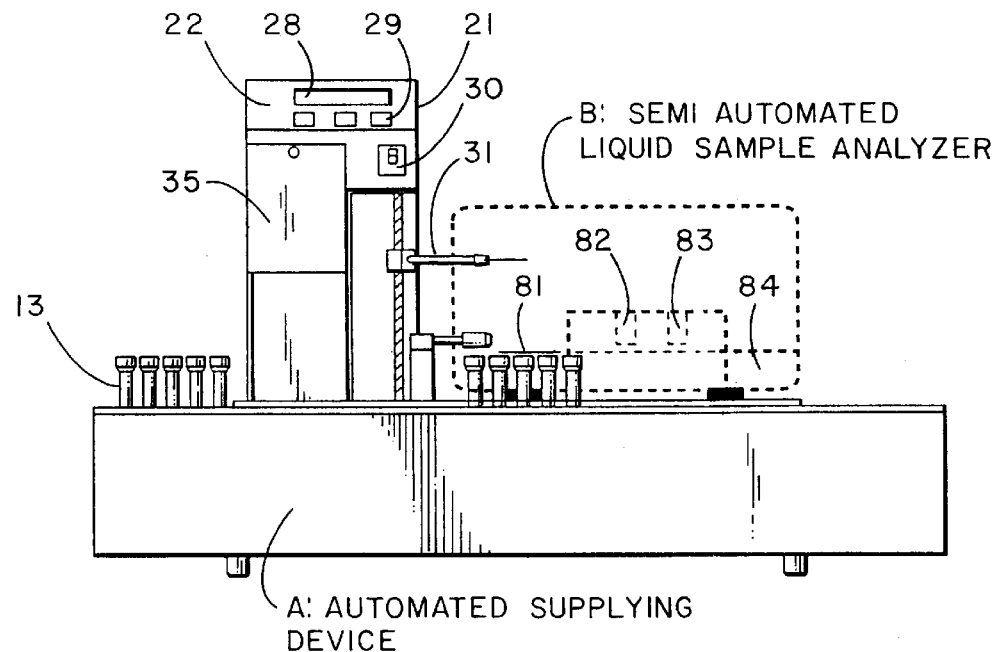
FIG. 1 is a front view of an embodiment of the present invention, wherein the device of the present invention is shown by a solid line and a semi-automated analyzer which is a parent device to be used in combination with the device of the present invention is shown by a thick dotted line.
Figure 2:
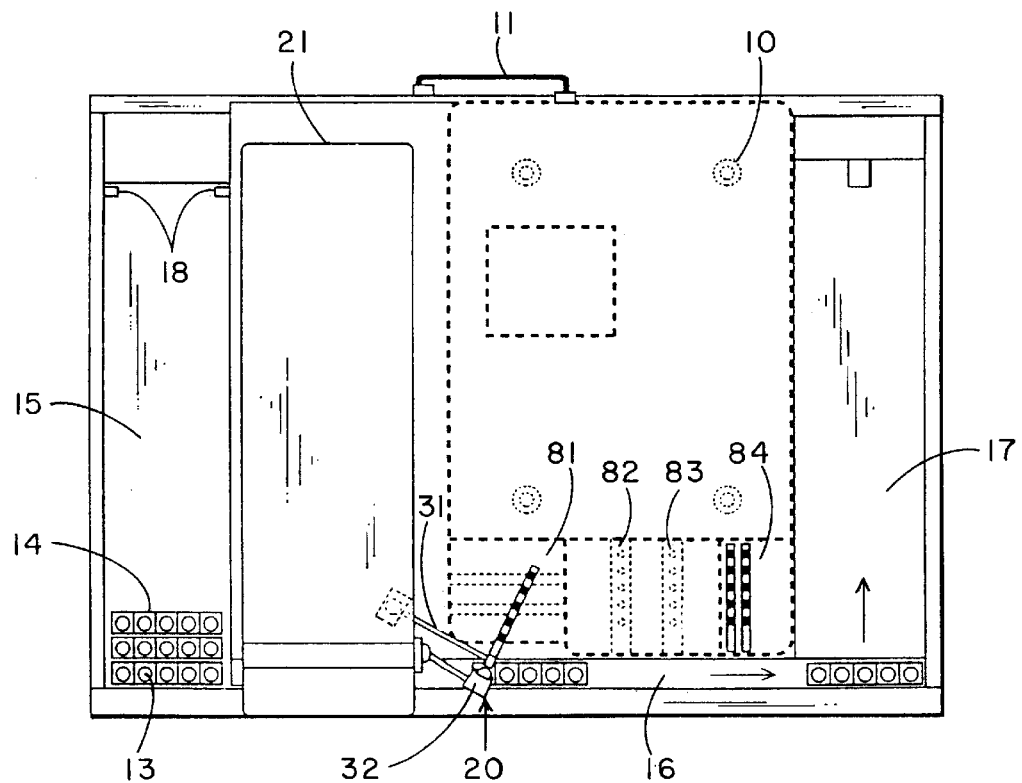
FIG. 2 is a plane view of an embodiment of the present invention, showing mechanical arrangements and electric connections of both devices.
Figure 3:
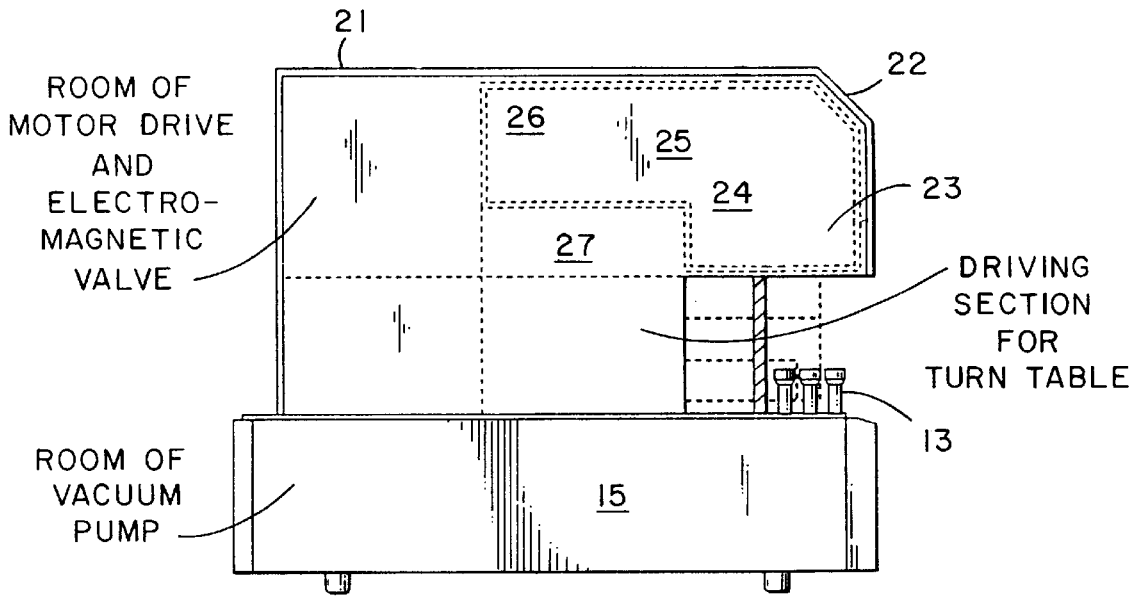
FIG. 3 is a side view of an embodiment of the present invention, wherein arrangement of internal constitution is shown by a dotted line block.
Figure 4:
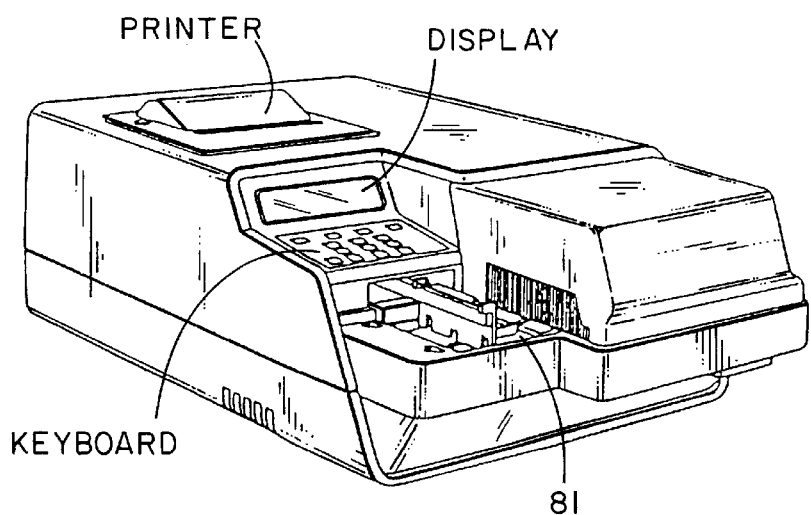
FIG. 4 is an illustrative perspective view of a semi-automated analyzer to be used in combination with the device of the present invention.
Figure 5:
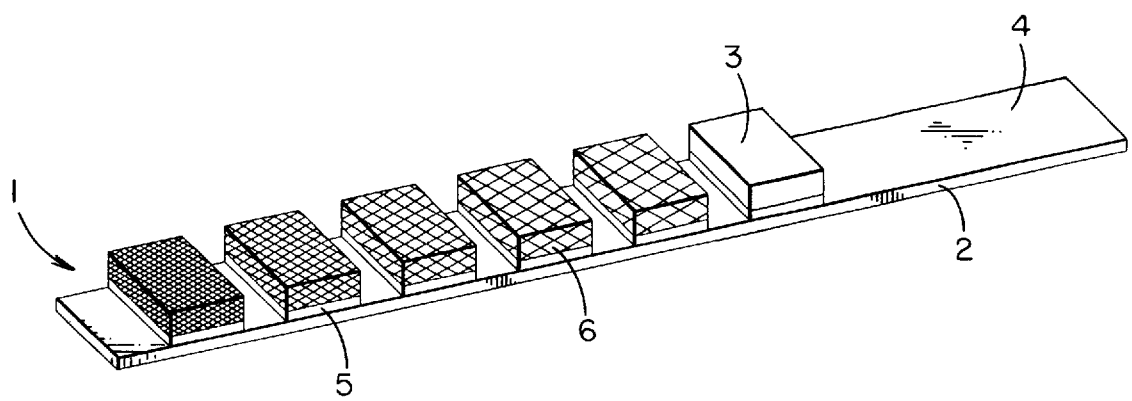
FIG. 5 is a view illustrating a schematic constitution of a test strip.

EXAMPLES (1) Relation between the device of the present invention and the parent device The portion shown by the solid line in FIGS. 1 to 3 is the auxiliary device of the present invention. The portion shown by the dotted line on a stand at the right side thereof is the parent device (the semi-automated analyzer illustrated by FIG. 4) to be aided by the device of the present invention for full automation.

Both devices are required to be positioned in relationship to each other such that "test strips after dipping in urine" supplied from the auxiliary device of the present invention may be received by a test strip receiving section of the parent device at a correct position and correct timing.

The positioning of the device of the present invention can be univocally determined by providing one or both of the devices with a positioning means 10 (e.g. a rubber pad and a receiving groove thereof). Alternatively, the univocal positioning may be achieved by providing guide members receiving at least two side walls of the parent device, respectively, on the stand of the device of the present invention.

The timing relationship of the parent device can be optimally achieved by, for example, programming an electronic control means (e.g. CPU) in the parent device such that the parent device may be switched by itself to either a semi-automated device or a fully automated device interlocked with an auxiliary device. An electronic control means of the auxiliary device of the present invention and the electronic control means in the parent device are connected by a specialized signal cable 11 such that both means may exchange information and a cooperation relation between supplying and transferring of liquid samples and test strips and the analyzer may be secured.

(2) Liquid sample transporting portion

Liquid samples (urine in this embodiment) are charged into test tubes 13 to a predetermined depth sufficient to dip all test pads 3 pasted on test strips 1. The test tubes 13 are placed in racks 14 each holding a suitable number, e.g. 5, of standing test tubes. Transportation of the test tubes by rack is carried out.

This transporting portion is disposed in a horizontal, U shape, which extends along the base of the stand on which the parent device is mounted, from the left side, the front to the right side. The transporting portion has a rack mounting portion 15, a front transporting portion 16 and a rack picking up portion 17.

On the rack mounting portion 15, for example, 20 of the specialized racks 14, i.e., 100 of the test tubes 13 can be set. The racks 14 mounted on the rack mounting portion 15 are successively pushed out on a transportation belt (not shown in the figures) of the front transporting portion 16 by claws 18 fixed to the left and right walls. The racks 14 are transported to a dipping and specimen weight detecting position 20 by the above belt which intermittently moves from the left to the right in an arrow direction.

Positioning of each test tube to the dipping position is carried out by detecting synchronous holes of the rack and controlling movement and stopping of the belt.

At the position 20, presence or absence of the test tubes 13 and the amounts of the liquid samples (specimens) are discriminated by a weight sensor prior to dipping. Further, reading of a bar code label or the like in which data specifying each test tube (i.e., the liquid sample which is contained therein) are recorded is also carried out at this position.

By reading the bar code label pasted on the side of the test tube 13 by a bar code label reading device disposed at the dipping position 20 and collating a read ID number with data of analytical results, data management can be carried out automatically.

The rack picking up portion 17 can contain, for example, 20 racks, i.e., 100 test tubes.

(3) Test tower

In the front view shown in FIG. 1, a tower portion at the left side of the stand is called a test tower 21.

The test tower 21 is explained also by referring to the internal arrangement shown in FIG. 3. The test tower 21 has an operation panel 22, a test strip bottle containing portion 23, a bottle driving mechanism 24 for picking up the test strips one by one from the test strip bottle, a drawing out mechanism 25 for picking up the test strips from the bottle driving mechanism 24, a right side discriminating mechanism 26 for facing pad surfaces of the test strips upward and a turntable mechanism 27 for transferring the test strips to a latter transfer means 31 (chuck arm).

The transfer means 31 (chuck arm) has a chuck for catching and holding the test strips being formed on its end and can move by turning upward and downward and in a horizontal plane on a leadscrew provided vertically.

A portion handling the test strips 1 is designed to enter into a chamber having airtightness (a frame shown by a double dotted line).

Figure 6:
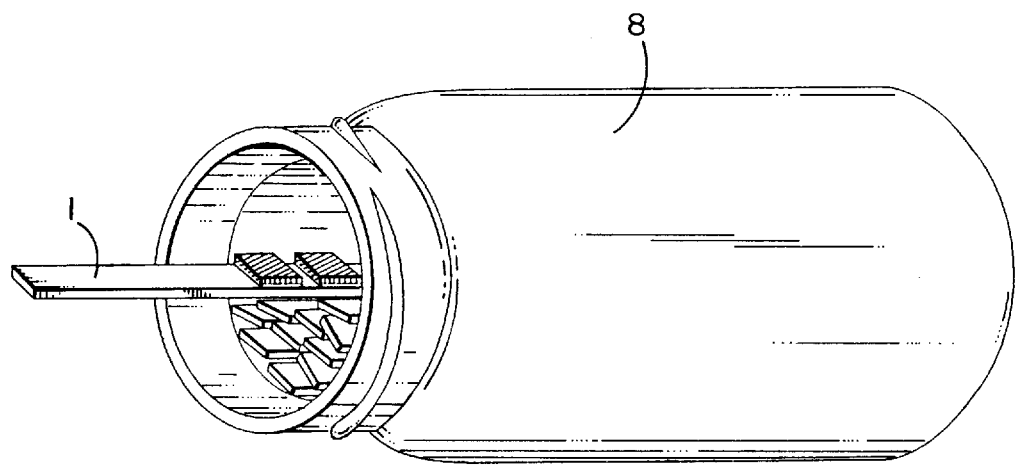
FIG. 6 is a view of a test strip bottle, showing both of a state that a plurality of test strips are contained and a state that one test strip is being drawn out.

In the airtight chamber, detection and movement of the test strips 1 are controlled by suction power of air (i.e., vacuum). The chamber is designed such that the air in the chamber may be circulated and replacement thereof with the outside air may be minimized. In order to prevent deterioration of the test pads on the test strips 1, the inner part of the chamber may be maintained at further low humidity by picking up the desiccant (not shown) contained in the test strip bottle 8 (see FIG. 6) and placing it in the chamber.

The test strips 1 contained in the test strip bottle 8 are picked up one by one by a pick up bar inserted into the inner part of the test strip bottle 8. The test strip 1 is sucked by an air chuck and drawn out on a test strip table. A suitable test strip pick-up mechanism for this purpose is disclosed, for example, in the Yokota et al. application Japanese Patent Application No. 119687/1994, filed concurrently herewith, which is incorporated by reference herein. The pad surface of the test strip 1 constantly face upward by a side discriminating mechanism 26, and the test strip 1 is placed on a turntable. A suitable means for discriminating the correct side of a test strip is disclosed, for example, in Yokota et al. application Japanese Patent Application No. 119737/1994, filed concurrently herewith, which is incorporated by reference herein. When urine charged into the test tube 13 in the rack 14 is transported to the dipping position 20, the turntable is turned 90° while lowering and transfers the test strip 1 to the transfer means 31 (chuck arm).

(4) Transfer means (chuck arm)

The transfer means 31 (chuck arm) catching the test strip 1 on the turntable is moved to above the waiting test tube 13 charged with urine at the dipping position 20 and waits instructions of dipping timing from the CLINITEK 200+. When the instructions are received, the test strip 1 is dipped in urine. When the test strip 1 is drawn up, excess urine on the test strip 1 is removed by an excess urine sucker 32 (sucker). The test strip 1 is placed on the stand at the receiving section 81 of CLINITEK 200+ and then drawn into the semi-automated analyzer, followed by analytical operations.

(5) Control means

The control means has a CPU board, a motor driver board, a power board, a LCD display board, a bar code reader, an electric capacitance type sensor for detecting a liquid level and various photosensors. As one example of CPU, uPD70108HC (an upper interchangeable CPU of V20/i8088) is used, and a control program is made by an assembler. The objects to be controlled are 13 stepping motors, 2 vacuum pumps, 6 electromagnetic valves, 3 systems of communication ports, a LCD display section 28, 3 key switches 29 and various sensors. The program is stored in 2 EP-ROM (27C512/64 KB). As one example of the stepping motors, there may be mentioned a programmable pulse generator, model PCL/MK (manufactured by Nihon Pulse Motor).

The part names and model numbers described above are only examples, and the present invention is not limited thereto.

(6) Operation panel

The operation panel 22 has the LCD display section 28, 3 of the key switches 29 and a power switch 30, and has a door 35 for containing and picking up the test strip bottle 8, being formed at a lower portion thereof.

(7) Operations

The door 35 for containing and picking up the test strip bottle 8 is opened, the cap of the test strip bottle 8 is opened, the test strip bottle 8 is inserted into the test strip bottle containing portion 23 with the opening of the test strip bottle 8 facing forward, and then the door 35 is closed. When the power switch 30 is turned on, both of the present device A and the parent device B are actuated (both devices are set in such a manner).

(8) Operation modes

There are 3 modes of "a basic mode" which is a mode used in a common measurement movement, "a parameter mode" which is a mode for setting measurement conditions and "a menu mode" which is a mode for all auxiliary functions of measurement. The modes can be selected by three of the key switches 29 on the operation panel 22.

When the power switch 30 is turned on, both of the auxiliary device of the present invention and the parent device (the semi-automated analyzer) are actuated. After electric and mechanical movements are confirmed by the basic mode, initialization is carried out, followed by subsequent routine operations for analysis.

In the parameter mode, for example, a standard value for checking a urine volume can optionally be set. The minimum urine volume required to be charged into a test tube varies depending on the kind of test pads (the number of items) and the kind of test tubes to be used. Thus, when the device is installed or the kind of test strips or test tubes is changed, it is necessary to set a standard value for checking a urine volume by using the parameter mode.

When a specimen having an insufficient urine volume is detected during measurement, subsequent movements can be instructed by the parameter mode.

The menu mode has 6 functions, for example, ① indication of a skipped tube (a function of specifying a specimen which is not measured because of an insufficient urine volume, after completion of analysis); ② indication of an empty bit (a function of searching a specimen which has a sufficient urine volume, but is not measured for some reason (an empty bit), after completion of analysis); ③ edition of tube number (a function of optionally setting tube number when measurement should be started with a specimen which is still not put in order being set at the dipping position for some reason); ④ direct erasing of unmeasured report (a function of erasing all reports of the unmeasured specimens described above when they are not necessary); ⑤ display of a status of the device (a function of displaying setting conditions of the device at that time on a screen); and ⑥ cleaning of the sucking portion (the sucker) (a function of daily cleaning the sucking portion itself and others after completion of measurement).

In the above description, urine is used as an example of the liquid samples to be analyzed, and the device B for analyzing urine is shown. However, the object to which the auxiliary function of the automated applying device A of the present invention is applied is not limited to a urine analyzer.

From the point that liquid samples and/or test strips cannot be supplied automatically and should be supplied manually, in a semi-automated test strip handling device, when test strips after dipping in liquid samples, supplied from the transfer means 31 of the automated supplying system of the present invention can be received at a correct position and movements can be controlled by movement timing of both devices, the automated supplying system of the present invention can be also applied to an analyzer for liquid samples (specimens) such as blood and saliva and can automate such an analyzer.

The present invention provides the supplying system as described above and achieves full automation of picking up test strips and/or liquid samples, dipping the test strips and supplying them to a semi-automated analyzer to extremely shorten actual working hours of an operator fully engaged with the above handling, thereby obtaining high efficiency, high precision and standardization of clinical tests.

We claim:

1. An automated supply instrument for supplying liquid sample treated test strips to an analyzer, said instrument having a receiving section which receives a test strip dipped in liquid sample, a section at which optical characteristics of test pads provided on the test strip are measured, and means for calculating analytical results based on the respective optical characteristics obtained by said measurement, which instrument comprises:

horizontal, u-shaped transportation means for passing a plurality of specimen containers containing liquid samples across a test strip dipping position;

transfer means including a pick-up bar for picking up and removing a test strip from an opening in one end of a test strip container containing a plurality of test strips by inserting said pick-up bar into said test strip container, conveying the test strip to the test strip dipping position, dipping the test strip in a specimen container containing liquid sample to thereby contact test pads; on the test strip with the liquid sample, drawing the test strip out of said specimen container after dipping, and then transferring the test strip to a receiving section of the analyzer; and means for controlling operation timing between movement of the u-shaped transportation means and movement of the transfer means.

2. The instrument of claim 1 which also contains turning means for confirming the side of a test strip containing test pads and turning the test strip such that the test pads face upward when the test strip is transferred to the receiving section of the analyzer.

3. The instrument of claim 1 which also contains sucking means for removing excess sample from a test strip after dipping the test strip in liquid sample.

* * * * *